United States Patent [19]

Bellus et al.

[11] 4,129,573

[45] Dec. 12, 1978

[54] COMPOSITIONS FOR AND METHOD OF INFLUENCING PLANT GROWTH AND NOVEL 1-PHENYL-2-OXO-PYRROLIDINE-4-CARBOXYLIC ACID DERIVATIVES

[75] Inventors: Daniel Bellus, Riehen; Werner Föry, Basel; Hans Tobler, Allschwil, all of Switzerland

[73] Assignee: Ciba-Geigy Corporation, Ardsley, N.Y.

[21] Appl. No.: 736,656

[22] Filed: Oct. 28, 1976

[30] Foreign Application Priority Data

Nov. 7, 1975 [CH] Switzerland .................. 14427/75

[51] Int. Cl.$^2$ .................. C07D 207/26; A01N 9/22
[52] U.S. Cl. .................. 260/326.45; 260/326.36; 260/326.5 FL; 260/326.5 S
[58] Field of Search .................. 260/326.45, 326.5 FL, 260/326.55, 326.36; 71/95

[56] References Cited

U.S. PATENT DOCUMENTS

| | | | |
|---|---|---|---|
| 2,757,125 | 7/1956 | Mudrah | 260/326.4 S |
| 2,811,496 | 10/1957 | Knuth | 260/326.4 S |
| 3,136,620 | 6/1964 | Bucha et al. | 260/326.4 S |
| 3,149,954 | 9/1964 | Harrod | 260/326.4 S |
| 3,238,223 | 3/1966 | Wilson et al. | 260/326.5 FL |
| 3,306,909 | 2/1967 | Uloth | 260/326.5 FL |
| 3,637,746 | 1/1972 | Wei et al. | 260/326.5 FL |
| 3,813,387 | 5/1974 | Pfirrmann et al. | 260/326.5 FL |
| 4,013,445 | 3/1977 | Bellus et al. | 260/326.4 S |
| 4,064,264 | 12/1977 | Nelson | 260/326.45 |

FOREIGN PATENT DOCUMENTS

| | | | |
|---|---|---|---|
| 218016 | 4/1961 | Austria | 260/326.45 |
| 1233278 | 12/1960 | France | 260/326.45 |
| 1053635 | 1967 | United Kingdom | 260/326.45 |
| 1323061 | 7/1973 | United Kingdom | 260/326.45 |

OTHER PUBLICATIONS

Pesson et al., Chem. Abs., vol. 74:87731p, (1971).

*Primary Examiner*—Donald G. Daus
*Assistant Examiner*—Mary C. Lee
*Attorney, Agent, or Firm*—Harry Falber

[57] ABSTRACT

This invention is directed to compositions for influencing plant growth, especially weed control, growth inhibition and desiccation, containing as active ingredient a 1-phenyl-2-oxo-pyrrolidine-4-carboxylic acid derivative of formula

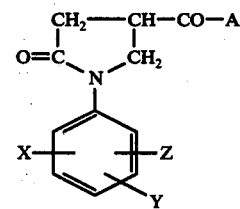

wherein A is $-OH$, $-OR_1$, $-SR_2$ or $-CN$, $R_1$ representing a cation or an ester moiety, $R_2$ an alkyl, benzyl or phenyl group, X being a substituent chosen from alkyl, alkoxy, alkylthio, phenoxy, substituted sulfamoyl or substituted sulfonylamino, Y is hydrogen, halogen, $CF_3$, alkyl, alkylthio or alkoxy and Z is hydrogen, alkyl, alkylthio or alkoxy.

The invention is also concerned with novel compounds of this formula, wherein Y is alkyl, alkylthio, halogen or $CF_3$.

3 Claims, No Drawings

COMPOSITIONS FOR AND METHOD OF INFLUENCING PLANT GROWTH AND NOVEL 1-PHENYL-2-OXO-PYRROLIDINE-4-CARBOXYLIC ACID DERIVATIVES

The present invention relates to plant growth-regulating compositions which contain 1-phenyl-2-oxo-pyrrolidine-4-carboxylic acids or derivatives thereof as active component, and to a method of regulating plant growth. The invention also relates to novel members of this group of active compounds and to a process for their manufacture.

The active components which form the basis of the compositions of the present invention have the formula I

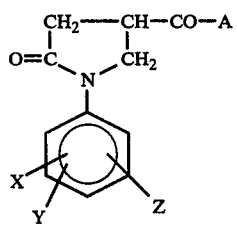

wherein

A represents a —OH, —OR$_1$, —SR$_2$ or —CN group,

R$_1$ represents the equivalent of a mono- to trivalent metal cation or of an inorganic or organic amine or quaternary ammonium cation, an unsubstituted or substituted alkyl group of 1 to 18 carbon atoms, an alkenyl, haloalkenyl, alkinyl or haloalkinyl group of 3 to 8 carbon atoms, a cycloalkyl group containing 3 to 12 ring carbon atoms, an unsubstituted or substituted phenyl, benzyl or phenylethyl group, R$_2$ represents an alkyl group of 1 to 6 carbon atoms, an unsubstituted or substituted benzyl or phenyl group, X represents an unsubstituted or substituted alkyl or alkoxy group of 1 to 4 carbon atoms, an alkylthio group of 1 to 4 carbon atoms, an optionally halogenated phenoxy group or one of the groups

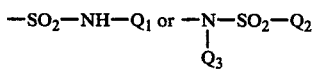

wherein

Q$_1$ represents a hydrogen atom, an unsubstituted or substituted alkyl group containing 1 to 6 carbon atoms in the alkyl chain, an alkoxy group of 1 to 4 carbon atoms, Q$_2$ represents an unsubstituted or substituted alkyl group containing 1 to 6 carbon atoms in the alkyl chain, in particular a haloalkyl group, such as CF$_3$, or an alkenyl group of 3 to 5 carbon atoms, and Q$_3$ represents a hydrogen atom or a lower alkyl group, Y represents a hydrogen atom, an alkyl, alkylthio or alkoxy group, each containing 1 to 4 carbon atoms, a halogen atom or a CF$_3$ group, and Z represents a hydrogen atom, an alkyl, alkylthio or alkoxy group, each containing 1 to 4 carbon atoms.

The invention also relates to those 1-phenyl-2-oxo-pyrrolidine-4-carboxylic acids and derivatives thereof of the narrower formula

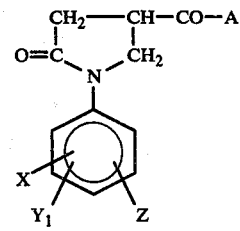

which are new, namely those wherein A, X and Z are as defined in formula I and Y$_1$ represents an alkyl or alkylthio group of 1 to 4 carbon atoms, a halogen atom or a CF$_3$ group, and to a process for the manufacture of these new derivatives.

The alkyl groups represented by the symbols R$_1$, R$_2$, X, Y, Y$_1$, Z and Q$_1$ to Q$_3$ can be straight-chain or branched.

Substituted alkyl groups represented by R$_1$, X, Q$_1$ and/or Q$_2$ can contain as substituents for example 1 to 3 halogen atoms, in particular fluorine, chlorine or bromine atoms, hydroxyl, alkoxy, alkylthio, amino, mono- or dialkyl-substituted amino groups or a cyano, alkoxycarbonyl, carbamoyl, tetrahydrofuryl or tetrahydropyranyl group. The alkyl moieties of these substituents can contain 1 to 4, in particular 1 or 2, carbon atoms.

A substituted alkoxy group represented by X can be for example preferably the radical —OCF$_2$CHF$_2$.

Suitable examples of substituents of phenyl, benzyl or phenylethyl groups represented by R$_1$ or R$_2$ are: alkyl, alkoxy, alkylthio, N-alkylamino or N,N-dialkylamino groups, each containing 1 to 4 carbon atoms, halogen atoms, in particular chlorine or fluorine atoms, trifluoromethyl, amino and nitro groups.

Halogen substituents of alkenyl or alkinyl groups represented by R$_1$ are for example bromine, but primarily fluorine or chlorine atoms.

The substituent in 4-position is preferably one of the following groups:
—COOH;
—COOR$_1$,
  wherein R$_1$ represents an unsubstituted alkyl group of 1 to 6 carbon atoms, in particular a methyl or benzyl group;
—COSR$_2$,
  wherein R$_2$ represents an alkyl group of 1 to 4 carbon atoms.

In a further preferred embodiment, R$_1$ represents the sodium or potassium cation or the cation of an organic amine. Suitable metal cations R$_1$ are also those of alkaline earth metals, or zinc, copper or iron. If the cation is di- or tri-valent, then it will be understood that it is bound to the number of anions of the carboxylic acid of the formula I (—COO$^\ominus$) corresponding to the valency of the cation. The compound of the formula I then has 1/n cation of the valency n.

It has been observed that the nature of the substitution of the phenyl ring (X, Y, Z) exerts a certain influence on the biological activity of the compounds of the formula I.

Preferred *trisubstituted* compounds are those which are 2,4,6-trialkylated.

Preferred *disubstituted* compounds (wherein Z is hydrogen) are those whose substituents X and Y are selected from any of the groups halogen, alkyl and alkoxy. Advantageously, however, X and Y are not both halogen or both alkyl.

The preferred substituent X in monosubstituted compounds (wherein Y=Z=H) is a group —SO₂NH-alkyl, preferably in 4-position, or an alkyl group in 2-position.

A further preferred substituent X is —NH—SO₂—CH₃ and in particular —NH—SO₂—CF₃, which is advantageously in 3 or 4-position and in addition can be present as further substituent Y and Z, for example methyl or CF₃. Such compounds exhibit in particular a good fruit abscission action.

The compounds of the formulae I and Ia can be obtained in known manner by reacting an aniline of the formula II or IIa

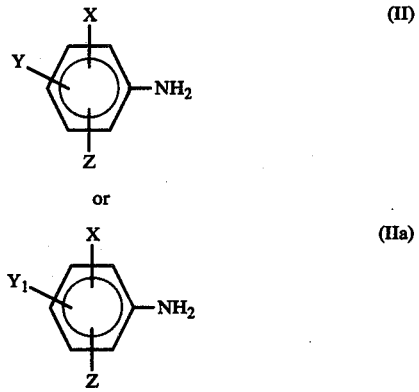

wherein X, Y, Y₁ and Z have the meanings already assigned to them above, with itaconic acid to give a compound of the formula I or Ia, wherein A represents the OH group, and the resultant 1-phenyl-2-oxo-pyrrolidine-4-carboxylic acid is optionally converted into another derivative as defined herein of the formula I or Ia.

The anilines of the formulae II and IIa are known per se or they can be obtained in conventional manner.

The reaction of the anilines of the formula II or IIa can be carried out in the melt, in aqueous, aqueous-organic or organic medium.

As suitable organic solvents it is possible to use for example aliphatic alcohols, such as methanol or ethanol, cyclic ethers, such as dioxan, aromatic hydrocarbons, such as benzene and toluene, or sulpholane, pyridine and pyridine bases. The reaction temperatures are in general between approx. 100° and 250° C.

The conversion of the 1-phenyl-2-oxo-pyrrolidine-4-carboxylic acids into derivatives as defined herein is also effected in known manner, for example:

Esters (A= —OR₁)

By reacting the free carboxylic acids with alkyl halides R₁-Hal in the presence of a base, by reacting the free carboxylic acids or the corresponding acid chlorides or fluorides with alcohols R₁OH or by transesterification.

Nitriles (A= —CN)

From acid halides and NaCN or KCN.

Thioesters (A = SR₂)

By reacting the acid chlorides or fluorides with mercaptans HSR₂.

Alkali metal salts, alkaline earth metal salts, Zn, Cu and Fe salts

By reacting the free carboxylic acids with hydroxides, alcoholates or carbonates of alkali metals or alkaline earth metals, such as sodium, potassium, lithium, calcium and magnesium hydroxide, sodium and potassium methylate and sodium and potassium ethylate, and reacting these alkali metal salts, in particular the sodium salts, with inorganic water-soluble zinc, copper and iron salts.

Ammonium and amine salts

By reacting the free carboxylic acid with ammonia, amines containing 1 or 2 nitrogen atoms or ammonium bases containing 1 to 2 nitrogen atoms, in a molar ratio of 1:1 or 2:1.

Esters of the formula I or Ia (A = OR₁) can also be obtained by a modified process by reacting an aniline of the formula II or IIa with an itaconic diester of the formula

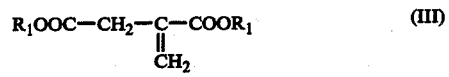

wherein R₁ is as defined above.

The reaction of the anilines with the itaconic diesters is advantageously carried out in the melt or in an inert organic solvent, for example an aliphatic alcohol, at temperatures between 100° and 250° C.

When the reaction is complete, the reaction products are isolated in the customary manner and purified, for example by reprecipitation or by filtering them off and recrystallising them from suitable solvents, such as diethyl ether, n-hexane or aliphatic alcohols containing 1 to 4 carbon atoms.

The following Examples illustrate the manufacture of a number of compounds of the present invention.

EXAMPLE 1

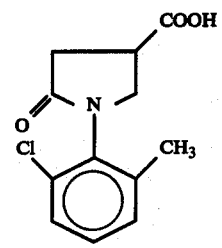

A mixture of 28.3 g (0.2 mole) of 2-methyl-6-chloroaniline and 27.3 g (0.21 mole) of itaconic acid is fused at 160° C. and kept at this temperature for 3 hours. The reaction mixture is cooled to 20° C. and treated, with stirring, with 300 ml of a mixture of diethyl ether and n-hexane (volume ratio 3:1). Yield: 39.4 g (78% of theory) of pure 1-(2-methyl-6-chlorophenyl)-2-oxo-pyrrolidine-4-carboxylic acid in the form of crystals.

Melting point: 168°–170° C.

Analysis for C₁₂H₁₂ClNO₃ (molecular weight 253.68): calculated C 55.71% H 4.77% Cl 14.0% N 5.53% found C 55.60% H 4.80% Cl 13.85% N 5.60%.

EXAMPLE 2

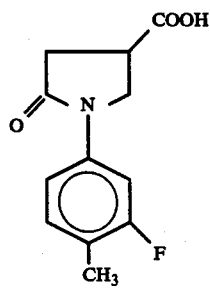

A solution of 6.25 g (0.05 mole) of 4-methyl-3-fluoroaniline and 6.5 g (0.05 mole) of itaconic acid in 70 ml of water is refluxed for 18 hours. After the reaction mixture has cooled to 20° C., the precipitated product is collected by filtration and dissolved in 50 ml of 2 N sodium hydroxide solution. This solution is extracted twice with diethyl ether. The aqueous phase is acidified (pH value approx. 1) with HCl. The precipitated crystals are collected by filtration, dried, and recrystallised from ethanol to yield 9.3 g (79% of theory) of pure 1-(methyl-3-fluorophenyl)-2-oxo-pyrrolidine-4-carboxylic acid which melts at 155°–160° C.

Analysis for $C_{12}H_{12}FNO_3$ (molecular weight 237.24): calculated C 60.80% H 5.10% F 8.02% N 5.91% found C 60.81% H 5.30% F 7.81% N 5.77%.

EXAMPLES 3 to 142

The compounds of the formula I listed in the following table were obtained by carrying out the procedure as described in Examples 1 and 2.

| Example | A | X | Y | Z | Melting point in ° C |
|---|---|---|---|---|---|
| 3 | OH | 2-OCH$_3$ | H | H | 132–134° |
| 4 | OH | 3-OCH$_3$ | H | H | 150–152° |
| 5 | OH | 4-OCH$_3$ | H | H | 157–160° |
| 6 | OH | 4-OC$_2$H$_5$ | H | H | 133–135° |
| 7 | OH | 2-CH$_3$ | 6-CH$_3$ | H | 149–151° |
| 8 | OH | 4-C$_2$H$_5$ | 3-Cl | H | 97–100° |
| 9 | OH | 4-C$_3$H$_7$(iso) | 3-Cl | H | 75–78° |
| 10 | OH | 4OC$_2$H$_5$ | 3-Cl | H | 128–130° |
| 11 | OH | 4-C$_3$H$_7$(iso) | H | H | 144–145° |
| 12 | OH | 3-SCH$_3$ | H | H | 133° |
| 13 | OH | 4-SCH$_3$ | H | H | 173–175° |
| 14 | OH | 2-C$_2$H$_5$ | 6-CH$_3$ | H | 149° |
| 15 | OH | 2-C$_2$H$_5$ | 6-C$_2$H$_5$ | H | 95–98° |
| 16 | —OCH$_3$ | 2-C$_2$H$_5$ | 6-C$_2$H$_5$ | H | n$_D^{20}$=1.5293 |
| 17 | OH | 4-C$_4$H$_9$(n) | H | H | 130–133° |
| 18 | OH | 4-C$_4$H$_9$(sec) | H | H | 117–118° |
| 19 | OH | 4-OC$_4$H$_9$ | H | H | 121–125° |
| 20 | OH | 2-OCH$_3$ | 5-OCH$_3$ | H | 63–69° |
| 21 | OH | 3-OCH$_3$ | 4-CH$_3$ | H | 147–149° |
| 22 | —OCH$_3$ | 6-CH$_3$ | 2-Cl | H | 168–170° |
| 23 | OH | 3-CH$_3$ | 5-CH$_3$ | H | 170–173° |
| 24 | OH | 4-CH$_3$ | 3-J | H | 149–152° |
| 25 | OH | 3-CH$_3$ | 4-CH$_3$ | H | 169–171° |
| 26 | OH | 4-CH$_3$ | 3-Cl | H | 144–145° |
| 27 | OH | 5-CH$_3$ | 2-Br | H | 165–168° |
| 28 | OH | 2-CH$_3$ | 5-CH$_3$ | H | 138–141° |
| 29 | OH | 3-CH$_3$ | H | H | 129–141° |
| 30 | OH | 3-C$_2$H$_5$ | H | H | 114–116° |
| 31 | OH | 3-SO$_2$NH$_2$ | H | H | 141–142° |
| 32 | OH | 4-SO$_2$NH(CH$_2$)$_3$OCH$_3$ | H | H | 105–107° |
| 33 | OH | 4-SO$_2$NH—CH(C$_2$H$_5$)$_2$ | H | H | 140–149° |
| 34 | OH | 2-CH$_3$ | 4-CH$_3$ | 5-CH$_3$ | 117–119° |
| 35 | OH | 4-SO$_2$NH$_2$ | H | H | 187–191° |
| 36 | OH | 4-SO$_2$NHC$_2$H$_5$ | H | H | 196–199° |
| 37 | OH | 4-O—⟨C$_6$H$_4$⟩—Cl | H | H | 72° |
| 38 | OH | 2-CH$_3$ | 3-CH$_3$ | H | 215° |
| 39 | OH | 4-O—⟨C$_6$H$_3$(Cl)⟩—Cl | H | H | 157–158° |
| 40 | —OCH$_3$ | 4-O—⟨C$_6$H$_3$(Cl)⟩—Cl | H | H | 75–77° |

Compounds having the structure

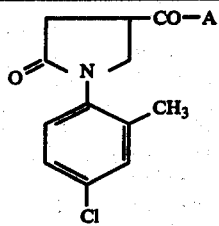

X = 2-CH$_3$
Y = 4-Cl
Z = H

| Example | A | Physical data (m.p., n$_D$ etc.) |
|---|---|---|
| 41 | OH | m.p. 79° |
| 42 | —OCH$_3$ | n$_D^{20}$ = 1.5452 |
| 43 | —OCH$_2$—CH=CH$_2$ | n$_D^{20}$ = 1.5468 |
| 44 | —O—C$_8$H$_{17}$ | n$_D^{20}$ = 1.5094 |
| 45 | —OCH$_2$—C$_6$H$_4$—CH$_3$ | n$_D^{20}$ = 1.5722 |
| 46 | —O—(CH$_2$)$_6$—Cl | n$_D^{20}$ = 1.5349 |
| 47 | —O—CH$_2$—C$_6$H$_5$ | n$_D^{20}$ = 1.5740 |
| 48 | —O—CH$_2$—CH=C(Cl)—CH$_3$ | n$_D^{20}$ = 1.5381 |
| 49 | —O—CH$_2$—CH$_2$—Br | n$_D^{20}$ = 1.5221 |
| 50 | —OCH$_2$—CH$_2$—OCH$_3$ | n$_D^{20}$ = 1.5384 |
| 51 | —O—CH$_2$-tetrahydrofuryl | n$_D^{20}$ = 1.5457 |

| Example | A | X | Y | Z | Physical constants (m.p. in °C; n$_D$) |
|---|---|---|---|---|---|
| 52 | OH | 3-OCH$_3$ | 5-OCH$_3$ | H | m.p. 122–127° |
| 53 | —OCH$_3$ | 3-OCH$_3$ | 5-OCH$_3$ | H | n$_D$ = 1.5505 |
| 54 | —O—C$_8$H$_{17}$ | 3-OCH$_3$ | 5-OCH$_3$ | H | n$_D$ = 1.4885 |
| 55 | —O-Benzyl | 3-OCH$_3$ | 5-OCH$_3$ | H | n$_D$ = 1.5747 |
| 56 | OH | 2-CH$_3$ | 3-Cl | H | m.p. 185° |
| 57 | —OCH$_3$ | 2-CH$_3$ | 3-Cl | H | n$_D^{20}$ = 1.5491 |
| 58 | —O—CH$_2$—CH=C(Cl)—CH$_3$ | 2-CH$_3$ | 3-Cl | H | n$_D$ = 1.5409 |
| 59 | —O—CH$_2$—CH$_2$—OCH$_3$ | 2-CH$_3$ | 3-Cl | H | n$_D$ = 1.5374 |
| 60 | OH | 4-OCH$_3$ | 3-Cl | H | m.p. 146–147° |
| 61 | —OCH$_3$ | 4-OCH$_3$ | 3-Cl | H | m.p. 76–78° |
| 62 | OH | 2-CH$_3$ | 5-Cl | H | m.p. 136–137° |
| 63 | —OCH$_3$ | 2-CH$_3$ | 5-Cl | H | n$_D$ = 1.5500 |
| 64 | OH | 3-CH$_3$ | 4-F | H | m.p. 133–134° |
| 65 | —OCH$_3$ | 3-CH$_3$ | 4-F | H | |
| 66 | —O—(CH$_2$)$_5$—CH$_2$Cl | 3-CH$_3$ | 4-F | H | |
| 67 | OH | 4-CH$_3$ | 2-Cl | H | m.p. 151° |
| 68 | —OCH$_3$ | 4-CH$_3$ | 2-Cl | H | n$_D$ = 1.5420 |
| 69 | OH | 2-CH$_3$ | 5-F | H | m.p. 156–159° |
| 70 | —OCH$_3$ | 2-CH$_3$ | 5-F | H | |
| 71 | —O—C$_8$H$_{17}$ | 2-CH$_3$ | 5-F | H | |
| 72 | —O—CH$_2$-tetrahydrofuryl | 2-CH$_3$ | 5-F | H | m.p. 153° |
| 73 | OH | 2-OCH$_3$ | 3-Cl | H | m.p. 153° |
| 74 | —OCH$_3$ | 2-OCH$_3$ | 3-Cl | H | n$_D$ = 1.5441 |
| 75 | —OCH(C$_2$H$_5$)$_2$ | 2-OCH$_3$ | 3-Cl | H | n$_D$ = 1.5202 |
| 76 | —OCH$_2$CH$_2$OCH$_3$ | 2-OCH$_3$ | 3-Cl | H | n$_D$ = 1.5351 |
| 77 | —O—CH$_2$—CH$_2$Br | 2-OCH$_3$ | 3-Cl | H | n$_D$ = 1.5613 |
| 78 | OH | 2-CH$_3$ | H | H | m.p. 151–160° |
| 79 | —OCH$_3$ | 2-CH$_3$ | H | H | n$_D$ = 1.5302 |
| 80 | —OH | 2-isoC$_3$H$_7$ | H | H | m.p. 75–78° |
| 81 | —OCH$_3$ | 2-isoC$_3$H$_7$ | H | H | n$_D$ = 1.5263 |
| 82 | —OCH$_2$CH$_2$OCH$_3$ | 2-isoC$_3$H$_7$ | H | H | n$_D$ = 1.5198 |
| 83 | OH | 2-C$_2$H$_5$ | H | H | 105–108° |
| 84 | —OCH$_3$ | 2-C$_2$H$_5$ | H | H | n$_D^{20}$ = 1.5319 |
| 85 | OH | 4-SO$_2$NH—C$_3$H$_7$(iso) | H | H | 185–188° |
| 86 | —OCH$_3$ | 4-SO$_2$NH—C$_3$H$_7$(iso) | H | H | 122–125° |
| 87 | OH | 2-OCH$_3$ | 5-Cl | H | 192–194° |
| 88 | —OCH$_3$ | 2-OCH$_3$ | 5-Cl | H | n$_D$ = 1.5519 |
| 89 | —O—CH$_2$—CH=CH$_2$ | 2-OCH$_3$ | 5-Cl | H | n$_D$ = 1.5479 |
| 90 | —O—CH$_2$—C$_6$H$_4$—CH$_3$ | 2-OCH$_3$ | 5-Cl | H | n$_D$ = 1.5695 |
| 91 | OH | 2-CH$_3$ | 4-CH$_3$ | 6-CH$_3$ | 147–150° |
| 92 | —OCH$_3$ | 2-CH$_3$ | 4-CH$_3$ | 6-CH$_3$ | 62–64° |
| 93 | —O—CH$_2$CH$_2$SCH$_3$ | 2-CH$_3$ | 4-CH$_3$ | 6-CH$_3$ | |

Compounds having the structure

| Example | A | Physical constants (m.p. in °C, nD) |
|---|---|---|
| 94 | OH | m.p. 117–120° |
| 95 | $H_2N^\oplus(C_2H_4OH)_2$ | viscous oil |
| 96 | —OCH$_3$ | viscous oil |
| 97 | O—C$_8$H$_{17}$ | m.p. 110–120° |
| 98 | —O—CH(C$_2$H$_5$)$_2$ | |
| 99 | —O—CH$_2$—CH=CH$_2$ | 60–65° |
| 100 | —O—CH$_2$—C≡CH | 35–40° |
| 101 | —O—CH$_2$—CH=C(Cl)—CH$_3$ | 77–80° |
| 102 | —O—CH$_2$—CH$_2$Br | 81–85° |
| 103 | —O—(CH$_2$)$_5$—CH$_2$Cl | 84–87° |
| 104 | —O—CH$_2$—CH$_2$—OCH$_3$ | 100–105° |
| 105 | —O—CH$_2$—CH(CH$_3$)$_2$ | 97–102° |
| 106 | —O—CH$_2$—CH$_2$—N(CH$_3$)$_2$ | 67–70° |
| 107 | —O—CH$_2$—CH$_2$—CN | |
| 108 | —O-Benzyl | 97–100° |
| 109 | —O—(CH$_2$)$_3$—O—C$_2$H$_5$ | 51–57° |
| 110 | —O—CH$_2$-cyclohexyl | 64–68° |
| 111 | —O—CH$_2$—CCl$_3$ | 115–120° |

Compounds having the structure

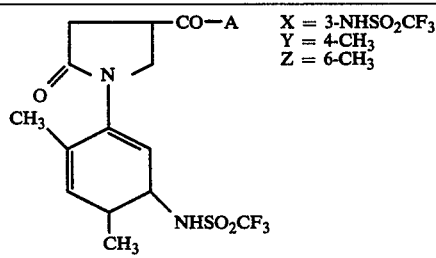

X = 3-NHSO$_2$CF$_3$
Y = 4-CH$_3$
Z = 6-CH$_3$

| Example | A | Physical constants |
|---|---|---|
| 112 | OH | 132–134° |
| 113 | $H_2N^\oplus(C_2H_4OH)_2$ | viscous oil |
| 114 | —OCH$_3$ | 168–171° |
| 115 | —O—CH$_2$-(tetrahydrofuryl) | 140–145° |
| 116 | —O-Benzyl | 112–118° |
| 117 | —O—CH(CH$_3$)—COOC$_2$H$_5$ | 99–101° |
| 118 | —O—CH$_2$—CH$_2$—N(CH$_3$) | 86–88° |
| 119 | —O—C$_8$H$_{17}$ | 156–160° |
| 120 | —O—CH$_2$—CH$_2$—CN | 157–61° |
| 121 | —O—CH$_2$—CH$_2$—O—CH$_3$ | 122–132° |

| Example | A | X | Y | Z | Physical data |
|---|---|---|---|---|---|
| 122 | OH | 3-NHSO$_2$CF$_3$ | 2-CH$_3$ | H | 83–85° |
| 123 | $H_2N^\oplus(C_2H_4OH)_2$ | 3-NHSO$_2$CF$_3$ | 2-CH$_3$ | H | viscous oil |
| 124 | —OCH$_3$ | 3-NHSO$_2$CF$_3$ | 2-CH$_3$ | H | viscous oil |
| 125 | —O—CH$_2$—CH$_2$—OCH$_3$ | 3-NHSO$_2$CF$_3$ | 2-CH$_3$ | H | 50–55° |
| 126 | —O—CH$_2$—CH=CH$_2$ | 3-NHSO$_2$CF$_3$ | 2-CH$_3$ | H | 153–155° |
| 127 | OH | 4-NHSO$_2$CF$_3$ | 3-CH$_3$ | H | 50–80° |
| 128 | $H_2N^\oplus(C_2H_4OH)_2$ | 4-NHSO$_2$CF$_3$ | 3-CH$_3$ | H | viscous oil |
| 129 | —O—CH$_2$—CH$_2$—Br | 4-NHSO$_2$CF$_3$ | 3-CH$_3$ | H | viscous oil |
| 130 | —O—C$_8$H$_{17}$ | 4-NHSO$_2$CF$_3$ | 3-CH$_3$ | H | viscous oil |
| 131 | —O—CH$_2$-(tetrahydrofuryl) | 4-NHSO$_2$CF$_3$ | 3-CH$_3$ | H | viscous oil |
| 132 | OH | 4-NHSO$_2$CF$_3$ | 3-CF$_3$ | H | |
| 133 | $H_2N^\oplus(C_2H_4OH)_2$ | 4-NHSO$_2$CF$_3$ | 3-CF$_3$ | H | |
| 134 | —OCH$_3$ | 4-NHSO$_2$—CF$_3$ | 3-CF$_3$ | H | |
| 135 | —O(CH$_2$)$_5$—CH$_2$Cl | 4-NHSO$_2$CF$_3$ | 3-CF$_3$ | H | |
| 136 | —O—CH$_2$-(tetrahydropyranyl) | 4-NHSO$_2$CF$_3$ | 3-CF$_3$ | H | |
| 137 | OH | 4-NHSO$_2$CH$_3$ | 3-CF$_3$ | H | |
| 138 | $H_2N^\oplus(C_2H_4OH)_2$ | 4-NHSO$_2$CH$_3$ | 3-CF$_3$ | H | |
| 139 | —O—C$_8$H$_{17}$ | 4-NHSO$_2$CH$_3$ | 3-CF$_3$ | H | |
| 140 | —O—CH$_2$—CH$_2$—OCH$_3$ | 4-NHSO$_2$CH$_3$ | 3-CF$_3$ | H | |
| 141 | —OCH$_3$ | 4-NHSO$_2$CH$_3$ | 3-CF$_3$ | H | |
| 142 | —O—CH$_2$—CH$_2$—F | 4-NHSO$_2$CH$_3$ | 3-CF$_3$ | H | | formula I and Ia are not phytotoxic to the emergent plants, but inhibit the growth in height of different plant species.

Compositions of the present invention, which contain as active component at least one compound of the formula I or Ia, are particularly suitable for inhibiting and controlling the growth of monocotyledonous and dicotyledonous plants, such as grasses, shrubs, trees, crops of cereals and leguminous plants, sugar cane, tobacco plants, soya, onion and potato tubers, ornamentals, fruit trees and vines.

A method of inhibiting plant growth is to be understood as meaning a control of natural plant development without effecting any change, in the sense of a mutation, in the life cycle of the plant which is determined by genetic features. By means of such a method it is possible to bring about artificially retarding phases in the plant development (growth in length, sucker formation, new growth, blossoming, fruit setting etc.). The method of growth regulation is applied at a period of plant development to be determined in each individual case.

The active components contained in the compositions of the present invention influence the plant growth in different ways. Thus they inhibit, delay or prevent primarily the growth and germination. When used in the customary rates of application, the compounds of the The active compounds of the formula I or Ia can be applied before or after the emergence of the plants, for example to the seeds or seedlings, to roots, tubers, stems, leaves, blossoms or other parts of plants, for example by applying the active compound itself or in the form of a composition to the plants and/or by treating the nutrient medium of the plant (soil).

The primary effect attained by the compounds of the formula I or Ia consists in the desired reduction of the plant size, in particular of the growth in height. In general, a certain change in the form of the plant is allied to this reduction in size. As a direct consequence of the reduction of the growth in height the plant is strengthened: leaves and stems are better developed. By shortening the distances between internodes in monocotyledonous plants the breaking strength is increased. In this way it is possible to prevent to a great extent harvest losses caused by thunderstorms, prolonged rainfall etc., which usually result in a storage of crops of cereals and leguminous plants, and thereby to facilitate harvesting. As side-effect, the reduced growth in height of useful plants results in a saving of fertilisers. This also applies equally to ornamental plants and ornamental grass plots, turf for sporting activities, grass-covered open spaces etc.

One of the greatest problems posed by pure grass cultivations, however, is the actual cutting of the grass itself, whether in open spaces of urban areas, industrial sites, playing fields, along main roads, on airport runways, on railway embankments or the embankments of water bodies. In all these cases it is necessary to cut the turf or grass periodically. This operation is not only time-consuming, complicated and expensive in respect of labour and machinery, but involves the personnel concerned and traffic users in considerable hazard.

For this reason there is an urgent need in areas with extensive traffic networks to maintain and tend the grassy covering for strengthening road shoulders and embankments on traffic routes on the one hand, and on the other to keep it at a reasonable height by simple means during the entire vegetation period. This need is fulfilled in a very advantageous manner by applying the compounds of the formula I.

In analogous fashion, the labour expended on cutting can be reduced by treating trees, shrubs and hedges, principally in urban and industrial areas, with the compounds of the present invention of the formula I or Ia.

The use of the active compounds of this invention of the formula I or Ia can also advantageously influence the growth of shoots and/or fertility of fruit trees and vines.

Ornamental plants of pronounced growth in length can be reared as compact potted plants by treating them with the active compounds of this invention.

The active compounds of the formula I or Ia are also useful for inhibiting the growth of undesired suckers, for example in tobacco and ornamental plants, whereby the labour-consuming detaching of these suckers by hand is avoided. They are also useful for inhibiting the formation of shoots in stored tubers, for example those of ornamental plants, onions and potatoes, and finally for increasing the yields of cultivated plants with marked vegetative growth, such as soya and sugar cane, by accelerating the transition from the vegetative to the generative growth phase by applying the active compounds of the invention.

Preferably the active compounds of the formula I or Ia are used to inhibit the growth of grasses, cereal crops, tobacco plants, soya and ornamental plants.

The compositions of this invention, however, can also be used for controlling weeds by the pre- or postemergence method in a variety of crops of cultivated plants, such as maize, rice, cotton, sorghum and lucernes etc., in particular for controlling the weeds *Avena fatua* and *Cyperus esculentus*.

The rates of application vary and depend on the time of application. In general they are between 0.1 and 5 kg of active compound per hectare for preemergence application and up to 4 kg per hectare fore treating existing crops.

Many of the active compounds of the formula I and the compositions containing them are also suitable for other forms of plant growth-regulating, in particular for facilitating fruit and leaf abscission through the formation of separation tissue on the fruit and leaf stems, which results in a substantial reduction in the force required to detach the fruit and consequently makes harvesting very much easier. A thinning out of blossoms and fruit also occurs in fruit trees.

The ease of fruit abscission in the mechanical and manual harvesting of olives and citrus fruit has become of great economic importance. Leaf abscission and defoliation is of importance in the harvesting of cotton.

The compositions according to the invention are obtained in known manner by intimately mixing and/or grinding active substances of the formula I or Ia with suitable carriers, with or without the addition of dispersants or solvents which are inert towards the active substances. The active substances may take and be used in the following forms:

Solid forms:
  dusts, tracking agents, granulates, coated granulates, impregnated granulates and homogeneous granulates.

Liquid forms:
  (a) active substance concentrates which are dispersible in water: wettable powders, pastes, emulsions:
  (b) solutions.

Solid forms (dusts, tracking agents, granulates), are obtained by mixing the active substances with solid carriers. Suitable carriers are, for example: kaolin, talc, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder residues of plant extractions, activated charcoal etc. These substances can either be used singly or in admixture with one another.

Granulates can be prepared by dissolving the active substances in an organic solvent and applying the resultant solution to a granulated material, for example attapulgite, $SiO_2$, granicalcium, bentonite etc., and then evaporating the solvent.

Polymer granules can also be prepared by impregnating a finished, porous polymer granulate, such as urea/formaldehyde polymers, polyacrylonitrile, and polyester, which have a specific surface area and a favourable predetermined adsorption/desorption ratio, with the active substances, for example in the form of their solutions (in a low boiling solvent) and removing the solvent. Polymer granules of this kind in the form of microgranules having a bulk density of 300 g/liter to 600 g/liter can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilize the active substance and/or nonionics, anionics and cationics, which, for example, improve the adhesion of the active ingredients on plants or parts of plants (tackifiers and agglutinants) and/or ensure a better wettability (wetting agents) and dispersibility (dispersing agents). Examples of suitable aggentinents are: olein/-chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl moiety, lignin sulphonic acids, the alkali metal and alkaline earth metal salts thereof, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of urea and formaldehyde, and also latex products.

Water-dispersible concentrates, i.e. wettable powders, pastes and emulsifiable concentrates, are compositions which can be diluted with water to the desired concentration. They consist of active substance, carrier, optionally additives which stabilize the active substance, surface-active substances and anti-foam agents and, if appropriate, solvents.

Wettable powders and pastes are obtained by mixing and grinding the active substances with dispersing agents and pulverulent carriers in suitable devices until homogeneity is attained. Suitable carriers are, for example, those already mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali metal, ammonium and alkaline earth metal salts of lignin sulphonic acid, in addition, alkylaryl sulphonates, alkali metal and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary acetalene glycols, dialkyl dilauryl ammonium chloride and fatty acid alkali metal and alkaline earth metal salts.

Suitable anti-foam agents are silicones.

The active substance is so mixed, ground sieved and strained with the additives mentioned above that, in wettable powders, the solid particle size of 0.02 to 0.04 mm and in pastes, of 0.03 mm, is not exceeded. Emulsion concentrates and pastes are manufactured by using dispersing agents, such as those cited previously above, organic solvents, and water. Examples of suitable solvents are: alcohols, benzene, xylenes, toluene, dimethyl sulphoxide, and mineral oil fractions which boil between 120° and 350° C. The solvents must be practically odourless, not phytotoxic, inert to the active substances and not readily inflammable.

Furthermore, the agents according to the invention can be applied in the form of solutions. For this purpose the active substances or several active substances of the formula I or Ia are dissolved in suitable organic solvents, mixtures of solvents or in water. Aliphatic and aromatic hydrocarbons, chlorinated derivatives thereof, alkylnaphthalenes and mineral oils, singly or in admixture, can be used as organic solvents. The compositions of this invention can be mixed with other biocidally active substances or agents. Thus in order to broaden the activity spectrum the compositions may contain, for example, insecticides, fungicides, bactericides, fungistats, bacteriostats or nematocides, in addition to the cited compounds of the formula I or Ia. The compositions of the invention may also contain plant fertilisers, trace elements etc.

The above described compositions contain between 0.1 and 95%, preferably between 1 and 80%, of active substance. Application forms can be diluted to a concentration as low as 0.001%. The rates of application are normally from 0.1 to 10 kg of active substance per hectare, preferably 0.25 to 5 kg per hectare. The active substances of the formula I or Ia can be formulated for example as follows. The parts denote parts by weight.

Dusts

The following substances are used to prepare
(a) 5% and
(b) a 2% dust:
  (a) 5 parts of 1-(2-methyl-4-chlorophenyl)-2-oxo-pyrrolidine-4-carboxylic acid,
  95 parts of talcum;
  (b) 2 parts of 1-(2,3-dimethylphenyl)-2-oxo-pyrrolidine-4-carboxylic acid,
  1 part of highly disperse silicic acid,
  97 parts of talcum.

The active substances are mixed with the carriers and ground.

Granules

The following substances are used to prepare 5% granules:
  5 parts of 1-(3,5-dimethoxyphenyl)-2-oxo-pyrrolidine-4-carboxylic acid
  0.25 parts of epichlorohydrin,
  0.25 parts of cetyl polyglycol ether,
  3.50 parts of polyethylene glycol,
  91 parts of kaolin (particle size 0.3–0.8 mm).

The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo.

Wettable powder

The following constituents are used to prepare
(a) a 50%,
(b) a 25% and
(c) a 10% wettable powder:
  (a) 50 parts of 1-(2,3-dimethylphenyl)-2-oxo-pyrrolidine-4-carboxylic acid,
  5 parts of sodium dibutylnaphthalene sulphate,
  3 parts of naphthalenesulphonic acid/phenolsulphonic acid/formaldehyde condensate (3:2:1),
  20 parts of kaolin,
  22 parts of Champagne chalk;
  (b) 25 parts of 1(2-bromo-5-methylphenyl)-2-oxo-pyrrolidine-4-carboxylic acid, 5 parts of sodium oleylmethyltauride,
2.5 parts of naphthalenesulphonic acid/formaldehyde condensate,
0.5 part of carboxymethyl cellulose,
5 parts of neutral potassium aluminium silicate,
62 parts of kaolin;
(c) 10 parts of 1-[3 -(S-trifluoromethyl-sulphonylamino]-2-oxo-pyrrolidine-4-carboxylic acid,
3 parts of a mixture of the sodium salts of saturated fatty alcohol sulphates,
5 parts of naphthalenesulphonic acid/formaldehyde condensate.
82 parts of kaolin.

The respective active substance is applied to the corresponding carriers (kaolin and chalk) and then these are mixed and ground, to yield wettable powders of excellent wettability and suspension powder. By diluting these wettable powders with water it is possible to obtain suspensions of the desired concentration of active substance. Such suspensions are used for controlling weeds and grass-like weeds in food crops by the preemergence method for treating areas of grass.

Paste

The following substances are used to prepare a 45% paste:
45 parts of 1[4-(N-isopropylsulphamoyl)-phenyl]-2-oxopyrrolidine-4-carboxylic acid,
5 parts of sodium aluminium silicate,
14 parts of cetyl polyglycol ether with 8 moles of ethylene oxide,
1 part of oleyl polyglycol ether with 5 moles of ethylene oxide,
2 parts of spindle oil,
10 parts of polyethylene glycol,
23 parts of water.

The active substance is intimately mixed with the additives in appropriate devices and ground. A paste is obtained from which, by dilution with water, it is possible to prepare suspensions of the desired concentration of active substance. The suspensions are suitable for treating areas of grass.

Emulsion Concentrate

The following ingredients are mixed to prepare a 25% emulsion concentrate:
25 parts of 1-(2-methoxy-3-chlorophenyl)-2-oxo-pyrrolidine-4-carboxylic acid,
5 parts of a mixture of nonylphenolpolyoxy-ethoxyethylene and calcium dodecylenesulphonate,
35 parts of 3,5,5-trimethyl-2-cyclohexan-1-one,
35 parts of dimethyl formamide.
This concentrate can be diluted with water to give emulsions in desired concentrations.

Instead of the respective active substance used in the preceding formulations, it is also possible to use another of the compounds comprised by the formula I.

We claim:
1. 1-Phenyl-2-oxo-pyrrolidine-4-carboxylic acids of the formula

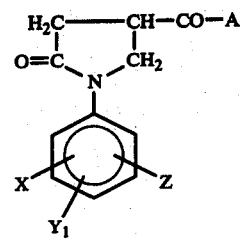

wherein
A is —OH, —OR$_1$, —SR$_2$ or —CN;
R$_1$ is an alkali metal, alkaline-earth metal, zinc, copper, iron or quaternary ammonium cation; C$_1$–C$_{18}$ alkyl or C$_1$–C$_{18}$ alkyl mono-to-tri-substituted by halogen, hydroxyl, alkoxy, alkylthio, amino, monoalkyl amino, dialkyl amino, cyano, alkoxycarbonyl, carbamoyl, tetrahydrofuryl or tetrahydropyranyl, the alkyl moieties of these substituents having 1–4 carbon atoms; C$_3$–C$_8$ alkenyl; C$_3$–C$_8$ haloalkenyl; C$_3$–C$_8$ alkynyl; C$_3$–C$_8$ haloalkynyl; C$_3$–C$_{12}$ cycloalkyl; phenyl, benzyl or phenylethyl, or phenyl, benzyl or phenylethyl substituted by alkyl, alkoxy, alkylthio, N-alkylamino, N,N-dialkylamino, halogen, trifluoromethyl, amino or nitro, the alkyl moieties of these substituents having 1–4 carbon atoms;
R$_2$ is C$_1$–C$_6$ alkyl, benzyl, phenyl, or benzyl and phenyl substituted by alkyl, alkoxy, alkylthio, N-alkylamino, N,N-dialkylamino, halogen, trifluoromethyl, amino or nitro, the alkyl moieties of these substituents having 1–4 carbon atoms;
X is —NH-SO$_2$CF$_3$ or —NH-SO$_2$CH$_3$ in the 3- or 4-position;
Y$_1$ is halogen, trifluoromethyl, C$_1$–C$_4$ alkyl or C$_1$–C$_4$ alkylthio; and
Z is hydrogen or C$_1$–C$_4$ alkyl.

2. A compound according to claim 1 of the formula

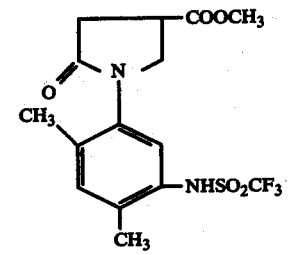

3. A compound according to claim 1 of the formula

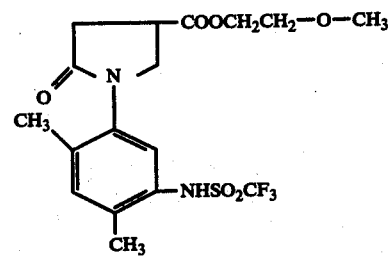

* * * * *